United States Patent [19]

Jacobi

[11] 3,937,809

[45] Feb. 10, 1976

[54] ADDITION COMPOUND OF A NUCLEOTIDE AND AN AMINO ACID AND THE USE THEREOF IN PROTECTION AGAINST ACTINIC RADIATION

[75] Inventor: Otto K. Jacobi, Wiesbaden-Igstadt, Germany

[73] Assignee: Kolmar Laboratories, Inc., Port Jervis, N.Y.

[22] Filed: May 1, 1974

[21] Appl. No.: 465,914

[52] U.S. Cl. ............... 424/60; 260/211.5 R; 424/59
[51] Int. Cl.² A61K 7/44; C07H 19/10; C07H 19/20
[58] Field of Search ........ 260/211.5 R; 424/180, 59, 424/60

[56] References Cited

UNITED STATES PATENTS

| | | | |
|---|---|---|---|
| 3,709,873 | 1/1973 | Fujimoto | 260/211.5 R |
| 3,803,116 | 4/1974 | Sekiguchi et al. | 260/211.5 R |
| 3,853,845 | 12/1974 | Rousseau et al. | 260/211.5 R |
| 3,892,844 | 7/1975 | Erlemann et al. | 424/59 |

*Primary Examiner*—Johnnie R. Brown
*Attorney, Agent, or Firm*—Andrus, Sceales, Starke & Sawall

[57] ABSTRACT

An addition compound of one mol of a nucleotide and 1 to 4 mols of an amino carboxylic acid or an amino sulfo acid. The compound is used as an agent for protection against actinic radiation.

7 Claims, No Drawings

ADDITION COMPOUND OF A NUCLEOTIDE AND AN AMINO ACID AND THE USE THEREOF IN PROTECTION AGAINST ACTINIC RADIATION

BACKGROUND OF THE INVENTION

Actinic radiation is a type of radiation which may induce chemical reactions. The ultraviolet portion of sunlight, for example, is an important actinic radiation. As the effect of actinic radiation on living organisms may be very harmful, all parts of the body which may be exposed to actinic radiation must be protected, and this is particularly true of human skin. In order to protect the skin against actinic radiation, it is common practice to apply preparations to the skin having agents which tend to essentially absorb the actinic radiation.

One well known compound for this purpose is, for example, p-aminobenzoic acid, but this compound has the serious drawback of showing insufficient absorption in the ultraviolet portion of the spectrum.

More recently purines and pyrimidines, as well as purine derivatives, such as the fluoro, chloro and methyl derivatives of purines, have been recommended as ultraviolet absorbing agents. However, these compounds do not show the degree of solubility which are required for the practical use of these compounds in protective preparations. Moreoever, they show only little absorption between 290 and 320 nm.

Even more important is the following phenomenon. It is known from radiation biology that ultraviolet radiation has a harmful effect on DNS and RNS. This results in the dimerization of two adjacent pyrimidine bases. This dimerization cannot be reversed by, for example, heat treatment. The most frequent dimer is the thymine dimer which may occur in the form of 6 possible isomers. The biological significance of the thymine dimers may be recognized by the fact that with decreasing survival rate of transformability of bacteria the number of dimers increases. Most recently, such ultraviolet damage has also been observed on human epidermic cells. The formation rate of dimers is at a maximum at 280 nm, whereas ultraviolet radiation at about 240 nm is capable of cleaving dimers which have already been formed. This is in agreement with the biological observation that the damage in bacterial DNS caused by radiation at 280nm may be reversed by a second radiation at 240 nm. Although the thymine dimers represent the most important and most frequent lethal damage caused by ultraviolet radiation, dimers of the other pyrimidines and other types of defects may play also an important role.

From the foregoing, it is evident that a protective agent against actinic radiation in the ultraviolet area should not only protect against the erythemae generating wave lengths between 290 nm and 315 nm, with an erythemae maximum at 300 nm, but should also shield against ultraviolet radiation at about 280 nm, while, on the other hanad, it should show the highest possible radiation transmittance at 240 nm. This would have the effect that erythemae and damage at the pyrimidine bases of the nycleic acids are prevented and at the same time the pyrimidine dimers which may already be formed are reversed.

SUMMARY OF THE INVENTION

This invention relates to a novel group of compounds having use as agents for protection against actinic radiation. The new compounds are stocheiometric addition compounds consisting of one mol of a nucleotide and one to four mols of an amino carboxylic acid of amino sulfo acid.

The compounds show strong absorption of ultraviolet radiation up to about 320 nm and although showing strong absorption in the ultraviolet area and particularly at about 280 nm, nevertheless, show a minimum of absorption at about 240 nm which is completely unexpected.

As a further advantage, the compounds are akin to the skin cells i.e., compatible with the skin, and show sufficient water solubility so that they can incorporated in aqueous skin protective compositions.

DESCRIPTION OF THE PREFERRED EMBODIMENT

The new compounds of the present invention are stoicheiometric addition compounds of one mol of a nucleotide and one to four mols of an amino carboxylic acid or an amino sulfo acid.

The nucleotide may be any of the known nucleotides. Nucleotides are the phosphoric acid esters of N-glycosides of purines or pyrimidines, such as adenine, guanine, cytosine, uracil or thymine. As an example, the sodium salt of adenosine-5'-diphosphoric acid may be described by the following formula:

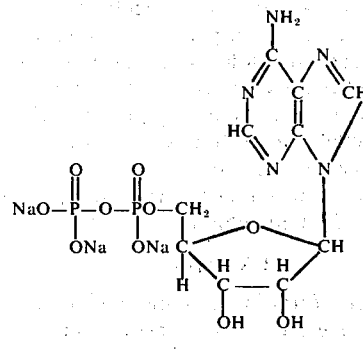

The nucloetides in the form of mono-,di-or tri-phosphates are natural products, but the nucleotides may also be made synthetically. Examples of mucleotides are: adenosine-5'-monophosphoric acid, adenosine-2'-diphosphoric acid, cytidine-3'-triphosphoric acid, uridine-3'-diphosphoric acid, guanosine-2-monophosphoric acid, uridine-5'monophosphoric acid sodium salt, cytidine-2'-triphosphoric acid, guanosine-5'-monophosphoric acid ammonium salt, etc.

In the above list water soluble salts, such as the ammonium and alkali metal salts, can be substituted for the acids.

The nucleotides, being natural products, are materials which are akin to the skin cells.

Since that part of a nucleotide which consists of a N-glycoside derived from a purine or a pyrimidine compound and a sugar, such as for example a pentose such as ribose, is called a nucleoside, the new compounds of the invention may be described by the following general formula:

[nucleoside . $(PO_3)_n$.$Me_{n+1}$]$AS_m$ wherein Nucleoside.$(PO_3)_n$.Me is a natural or synthetic nucleotide, Me is a hydrogen, alkali metal, ammonium or amine cation, $n$ is an integer from 1 to 3, $m$ is an integer from 1 to ($n$+1) and AS is an amino carboxylic acid or an amino sulfo acid or the alkali metal salt, ammonium salt, amine salt, or acid amide thereof.

The amino acids to be used in preparing the new compounds may be aliphatic, aromatic, naphthenic, or heterocyclic amino carboxylic or amino sulfo acids containing from 1 to 20 carbon atoms, and may also be substituted, for example by OH groups. They may contain carboxylic groups and sulfo groups at the same time. In addition, salts of the amino acids, such as the alkali metal salts, etc., can be used. Preferably, the amino acids are basic amino acids. According to a particular embodiment of the invention, the amino acids contained in one molecular compound of the invention are different from each other.

Examples of amino acids which may be contained in the molecular compounds according to the invention are as follows: o-aminobenzoic acid, p-aminobenzoic acid, amino salicylic acid, sulfanilic acid, 5-amino-5-sulfo salicylic acid, aminophenol sulfo acid, 1-amino-2-hydroxynaphthalene sulfate, Na-amino isophthalate, histidine, arginine, cystine, aminonaphtoic sulfo acid, etc.

The new compounds may be prepared by different methods. In general, separate solutions of the nucleotide and of the amino acid are prepared. The solvent for the nucleotide is preferably water. Also, for the amino acid, water is the preferred solvent, however, other solvents, such as acetone, have also been found to be very well suited.

The two solutions are mixed together. If a precipitate forms it is filtered off, suspended in water and is subsequently brought into solution again by the addition of alkali. From the solution thus formed, the new addition compound may be obtained by known methods, such as, for example, evaporation to dryness, application of vacuum, freeze drying, etc.

The following examples illustrate the preparation of compounds of the invention

EXAMPLE 1

Preparation of uridine-p-aminobenzoic acid:

1 mole uridine-5-monophosphoric acid is dissolved in 10 parts water. Separately, 2 moles n-aminobenzoic acid are dissolved in 90 parts anhydrous acetone, The solution of the uridine phosphoric acid is slowly added with stirring to the solution of the n-aminobenzoic acid. A precipitate forms which is filtered off and is dried at 40°C until it is free of acetone. Thereafter, the filter cake is suspended in water, and NaOH is added until the precitate dissolves. The solution of uridine-5'-monophosphoric acid-(p-Na-aminobenzoate)$_2$ is evaporated under reduced pressure. A white crystalline compound is obtained.

EXAMPLE 2

Preparation of adenosine-tryptophane:

1 mol adenosine-5'-monophosphoric acid is dissolved in 5 parts water. Separately, 2 mols tryptophane are dissolved in 5 parts water. Thereafter, the solution of the amino acid is poured into 9 parts of a 2:1 mixture of methanol and acetone. To this mixture the solution of the nucleotide is slowly added. A precipitate forms. This precipitate is filtered off and dried at 60°C. Then the precipitate is suspended in water. To the suspension the exact amount of NaOH is added to neutralize the free carboxylic groups of the tryptophane. The precipitate dissolves. The solution is evaporated under reduced pressure, and a white crystalline powder is obtained, which consists of adenosine-5'-monophosphoric acid-(Na-tryptophanate)$_2$.

EXAMPLE 3

Preparation of adenosine-5'-monophosphoric acid-(p-aminobenzoic acid-Na)$_2$.

1 mol of adenosine-5'-monophosphoric acid is dissolved in 5 parts water. 2 mols of p-aminobenzoic acid are dissolved in 9 parts of a mixture of methanol and water. The two solutions are slowly mixed with stirring. A precipitate forms, which is filtered off and dried at 60°C. Thereafter, the cake is suspended in water, and to the solution thus obtained NaOH is added in a sufficient amount to neutralize the carboxyl groups of the amino acid. The precipitate redissolves. The water is evaporated under reduced pressure, and a white, crystalline residue is obtained which consists of the desired molecular compound.

EXAMPLE 4

Preparation of guanosine-5'-diphosphoric acid-mono-Na-(3-amino-2-K-napthoate)-(5-diammonium-5-amino-3-sulfosalicylate).

4.63 g(0.01 mol) guanosine-5'-diphosphoric acid-mono-Na salt are dissolved in 100 ml distilled water, 2.25 g (0.01 mol) 3-amino-K-2-napthoate and 2.67 g(0.01 mol) 5-amino-3-sulfosalicylic acid diammonium salt are dissolved together in 200 ml distilled water, and this solution is added to the solution of the guanosine-5'-diphosphoric acid mono-Na salt. The solution is thoroughly stirred and is evaporated under reduced pressure. The crystal cake obtained may be recrystalized from water/propanol. The yield is 100%.

The following Table 1 lists additional compounds of the invention along with their physical properties.

TABLE I

| No. | Molecular Compound | Brutto Formula | M.W. | N(%) calc. | found | pH (c=0.005) | UV-spectrum | Extinction coefficients (c=0.005; d-l; water) mol.Ext.coeff. | E250/E260 | E280/E260 | E290/E260 |
|---|---|---|---|---|---|---|---|---|---|---|---|
| 1. | Uridine-5'-monophosphoric acid-(tryptophane)$_2$ | $C_{31}H_{37}N_6O_{13}P$ | 732.63 | 11.45 | 11.43 | 6.5 | $\lambda max=$ 233m$\mu$ | $\epsilon=278000\pm\lambda$ 4% | 0.77 | 0.69 | 1.51 |
| 2. | Adenosine-5'-monophosphoric acid-(Na-p-aminobenzoate)$_2$ | $C_{24}H_{26}N_7O_{11}PNa_2$ | 665.34 | 14.75 | 14.89 | 6.5 | $\lambda max=$ 265m$\mu$ | $\epsilon=253000\pm\lambda$ 4% | 0.89 | 0.70 | 0.4 |
| 3. | Uridine-5-Na-monophosphoric acid-(Na-p-aminobenzoate) | $C_{16}H_{18}N_3O_{11}PNa_2$ | 505.21 | 8.30 | 8.13 | 6.95 | $\lambda max=$ 206m$\mu$ | $\epsilon=173500\pm\lambda$ 4% | 0.79 | 0.71 | 0.32 |
| 4. | Uridine-5'-monophosphoric acid-(Na-histidine)$_2$ | $C_{15}H_{20}N_8O_{11}PNa_2$ | 676.47 | 16.55 | 16.85 | 7.0 | $\mu max=$ 210m$\mu$ | $\epsilon=156000\pm\lambda$ 4% | 0.75 | 0.42 | 0.09 |

TABLE I-continued

| No. | Compound | Brutto Formula | M.W. | N(%) calc. | found | pH (c=0.005) | UV-spectrum | Extinction coefficients (c=0.005; d-l; water) mol.Ext.coeff. | E250/E260 | E280/E260 | E290/E260 |
|---|---|---|---|---|---|---|---|---|---|---|---|
| 5. | Adenosine-5'-monophosphoric acid-(Na-tryptophane)$_2$ | $C_{32}H_{36}N_9O_{11}PNa_2$ | 799.68 | 15.8 | 15.07 | 7.0 | λmax= 220mμ | ε=320000±λ 4% | 0.76 | 0.67 | 0.33 |
| 6. | Uridine-5-monophosphoric acid-(Na-tryptophane)$_2$ | $C_{31}H_{25}N_6O_{13}$ | 776.59 | 10.8 | 10.53 | 7.25 | λmax= 222mμ | ε=329200±λ 4% | 0.71 | 0.76 | 0.30 |
| 7. | Adenosune-5'-monophosphoric acid-(o-Na-aminophenolsulfonate)$_2$ | $C_{22}H_{26}N_7O_{13}PNa_2S_2$ | 769.23 | 12.72 | 12.65 | 6.35 | λmax= 274mμ | ε=332000±λ 4% | 0.82 | 0.45 | 0.46 |
| 8. | Cytidine-5'-monophosphoric acid-(Na-o-aminophenol sulfonate)$_2$ | $C_{21}H_{26}N_5O_{16}PS_2Na_2$ | 745.57 | 9.39 | 9.04 | 6.60 | λmax= 215mμ | ε=298000±λ 4% | 1.41 | 1.07 | 0.69 |
| 9. | Adenosine-5'-monophosphoric acid-(Na-sulfanilate)$_2$ | $C_{22}H_{26}N_7O_{13}S_2PNa_2$ | 737.62 | 13.3 | 13.5 | 6.50 | λmax= 208mμ | ε=265500±λ 4% | 1.06 | 0.21 | 0.11 |
| 10. | Cytidine-5'-monophosphoric acid-(Na-tyrosine)$_2$ | $C_{27}H_{34}N_5O_{14}PNa_2$ | 729.39 | 9.65 | 9.50 | 6.65 | λmax= 224mμ | ε=189000±λ 4% | 0.75 | 1.15 | 0.40 |
| 11. | Uridine-5'-monophosphoric acid-(Na-tyrosine)$_2$ | $C_{27}H_{31}N_4O_{15}PNa_2$ | 728.35 | 7.43 | 7.80 | 7.05 | λmax= 224mμ | ε=164500±λ 4% | 0.64 | 0.62 | 0 |
| 12. | Cytidine-5'-monophosphoric acid-(Na-tryptophane)$_2$ | $C_{31}H_{36}N_7O_{12}PNa_2$ | 775.65 | 12.70 | 12.70 | 7.0 | λmax= 223mμ | ε=295500±λ 4% | 0.71 | 1.11 | 0.42 |
| 13. | Adenosine-5'-monophosphoric acid-(p-aminobenzoic acid)$_2$ | $C_{24}H_{28}N_7O_{11}P$ | 621.34 | 15.73 | 16.16 | 6.2 | λmax= 265mμ | ε=236000±4 | 0.82 | 0.89 | 0.57 |
| 14. | Cytidine-5'-Na-monophosphoric acid-(Na-p-amino-benzoic acid) | $C_{16}H_{19}N_4O_{12}PNa_2$ | 504.25 | 11.10 | 11.30 | 7.35 | λmax= 206mμ | ε=161000±λ 4% | 0.66 | 1.00 | 0.51 |
| 15. | Guanosine-5'-monophosphoric acid-(5-aminosulfosalicylate)$_2$ | $C_{24}H_{24}N_7O_{20}PS_2Na_4$ | 917.59 | 10.68 | 10.01 | 7.05 | λmax= 215mμ | ε=358000±λ 4% | 1.3 | 0.44 | 0.14 |
| 16. | Guanosine-5'-monophosphoric acid-(5-aminonaphthalene-1-sulfate)$_2$ | $C_{30}H_{30}N_7O_{14}PS_2Na_2$ | 853.73 | 11.48 | 11.18 | 6.85 | λmax= 210mμ | ε=333000±λ 4% | 1.86 | 0.47 | 0.31 |
| 17. | Guanosine-5'-monophosphoric acid (1-amino-2-hydroxy-naphthlene sulfate)$_2$ | $C_{30}H_{30}N_7O_{16}PS_2Na_2$ | 885.71 | 11.07 | 10.57 | 6.85 | λmax= 215mμ | ε=346000±λ 4% | 1.37 | 0.53 | 0.41 |
| 18. | Uridine-5'-monophosphoric acid-(p-amino benzoate)$_2$ | $C_{23}H_{25}N_4O_{12}PNa_2$ | 642.27 | 8.74 | 8.15 | 6.65 | λmax= 260mμ | ε=231000±λ 4% | 0.82 | 0.69 | 0.33 |
| 19. | Adenosine-5'-monophosphoric acid-Na-(p-aminobenzoate) | $C_{17}H_{20}N_6O_9PNa_2$ | 529.28 | 15.85 | 15.10 | 6.8 | λmax= 210mμ | ε=210500±λ 4% | 0.73 | 0.50 | 0.22 |
| 20. | Cytidine-5'-monophosphoric acid-(p-aminobenzoate)$_2$ | $C_{23}H_{26}N_5O_{12}PNa_2$ | 641.31 | 10.92 | 10.97 | 5.9 | λmax= 270mμ | ε=255500±λ 4% | | | 0.35 |
| 21. | Cytidine-5'-monophosphoric acid -Na-(p-aminobenzoate) | $C_{16}H_{19}N_4O_{12}PNa_2$ | 504.25 | 11.11 | 11.30 | 7.35 | λmax= 206mμ | ε=161000±λ 4% | 0.66 | 1.00 | 0.51 |
| 22. | Cytidine-5'-monophosphoric acid-Na-(p-aminobenzoate) | $C_{16}H_{18}N_3O_{11}PNa_2$ | 505.21 | 8.31 | 8.13 | 6.95 | λmax= 206mμ | ε=173500±λ 4% | 0.79 | 0.71 | 0.32 |

The following Table illustrates the ultraviolet absorption characteristics at wave lengths of 300 nm, 280 nm, and 240 nm for the compounds of the invention, as well as other known compounds which have been used in the past as sun protective agents.

TABLE 2

| Compound | UV Absorption in % | | |
|---|---|---|---|
| | 300 nm | 280 nm | 240 nm |
| 1. Adenine | 14 | 52 | 100 |
| 2. Cytosine | 95 | 98 | 100 |
| 3. Uracil | 42 | 45 | 90 |
| 4. Guanine | 11 | 62 | 73 |
| 5. Hypoxanthine | 6 | 65 | 100 |
| 6. p-Aminobenzoic acid | 100 | 100 | 91 |
| 7. p-Aminobenzoate | 94 | 100 | 95 |
| 8. o-Aminophenol sulfate | 72 | 70 | 98 |
| 9. Anthranilic acid(o-Aminobenzoic acid) | 84 | 48 | 99 |
| 10. 4-Aminosalicylic acid | 99 | 99 | 98.5 |
| 11. Salicylic acid | 94 | 74 | 98 |
| 12. 5-Amino-3-sulfosalicylic acid-$Na_2$ | 26 | 0 | 87 |
| 13. Adenosine-5'-monophosphoric acid-$Na_2$ | 6 | 8 | 80 |
| 14. Cytidine-5'-monophosphoric acid-$Na_2$ | 3 | 88 | 86 |
| 15. Uridine-5'-monophosphoric acid-$Na_2$ | 0 | 55 | 70 |
| 16. Uridine-5'-monophosphoric acid-(p-aminobenzoate)$_2$ | 76 | 99 | 79 |
| 17. Cytidine-5'-monophosphoric acid-(p-aminobenzoate)$_2$ | 98 | 100 | 78 |
| 18. Adenosine-5'-monophosphoric acid-(p-aminobenzoate)$_2$ | 99 | 100 | 73 |
| 19. Uridine-5'-monophosphoric acid-Na (p-aminobenzoic acid)Na | 52 | 95 | 77 |
| 20. Cytidine-5'-monophosphoric acid-Na-(p-aminobenzoate) | 73 | 97 | 78 |
| 21. Adenosine-5'-monophosphoric acid-Na-(p-aminobenzoic acid)Na | 65 | 90 | 77 |
| 22. Cytidine-5'-monophosphoric acid-(o-aminobenzoic acid)$_2Na_2$ | 55.5 | 79 | 98 |

As may be seen from Table 2, the purine, pyrimidines, nucleotides, as well as the usual ultraviolet protective agents show either too strong absoprtion at 240 nm, i.e. they prevent the reversion of the dimer formation, or they do not give sufficient protection at 300 nm of 280 nm, respectively, and thus, cannot prevent erythemae and dimer formation. The components of the invention, as illustrated by samples 16–21 in the Table, however, fulfill these requirements in a most surprising manner.

The following table illustrates the water solubility of compounds of the invention as compared with other known sun protective compounds.

TABLE 3:

| Solubility in Water at 20°C (%) | |
|---|---|
| 1. Adenine | 0.084 |
| 2. Cytosine | 0.400 |
| 3. Uracil | 0.200 |
| 4. Adenosine-5'-monophosphoric acid-(p-aminobenzoate)$_2$ | 1.00 |
| 5. Adenosine-5'-monophosphoric acid-Na-(p-aminobenzoate) | 4.00 |
| 6. Cytidine-5'-monophosphoric acid-(p-aminobenzoate)$_2$ | >10.00 |
| 7. Cytidine-5'-monophosphoric acid -Na-(p-aminobenzoate) | 1.00 |
| 8. Uridine-5'-monophosphoric acid-(p amino benzoate)$_2$ | 5.00 |
| 9. Uridine-5'-monophosphoric acid-Na-(P-aminobenzoate) | 9.20 |

The compounds may be used as new and extremely active agents for the protection against radiation, for which purpose they may be incorporated into aqueous or diluted alcoholic solutions, lotions, liquid or pasty emulsions and ointments. The compounds can be used in an amount of 0.1% to 99.9% by weight of the cosmetic or pharmaceutical composition.

The compounds find useful application for commercial skin protection, by light sensitive persons, in dermatology, as sun protective agents, as agents for the protection of genes and cells. The compounds of the invention may be combined with other known radiation protective agents, skin protecting agents and/or medicinal agents.

Examples of Skin preparations incorporating the compounds of the invention are as follows in weight percent.

Water Base Lotion:
  60% deionized water
  5% polyoxyethylene sorbitan fatty acid ester
  20% paraffinium liquidum
  5% petrolatum
  5% sorbitan fatty acid ester
  5% uridine-5'-monophosphoric acid-(p-aminobenzoic acid-Na)$_2$ Alcohol Base Lotion:
  40% ethyl alcohol
  57% deionized water
  3% adenosine-5'-monophosphoric acid-(p-aminobenzoic acid-Na)$_2$ Ointment:
  65% petrolatum
  34.5% lanolin
  0.5% adenosine-tryptophane Various modes of carrying out the invention are contemplated as being within the scope of the following claims particularly point out and distinctly claiming the subject matter which is regarded as the invention.

I claim:

1. A topical composition for protection against actinic radiation, comprising a dermatologically acceptable inert carrier suitable for application to human skin, and having dispersed therein from 0.1% to 99.9% by weight of a compound of the formula:

[Nucleoside $(PO_3)_n \cdot Me_{n+1}$]$AS_m$ wherein the nucleoside is a glycoside of a compound selected from the group consisting of adenine, guanine, cytosine, uracil and thymine; Me is a cation selected from the group consisting of hydrogen, an alkali metal, and ammonium; $n$ is an integer from 1 to 3; $m$ is an integer from 1 to ($n + 1$); and AS is acid having from 1 to 20 carbon atoms and selected from the group consisting of an amino carboxylic acid and an amino sulfo acid.

2. The composition of claim 1, wherein the dermatologically acceptable inert carrier is an aqueous solution.

3. The composition of claim 1, wherein AS is selected from the group consisting of an alkali metal salt of an amino carboxylic acid, an alkali metal salt of an amino sulfo acid, an ammonium salt of an amino carboxylic acid and an ammonium salt of an amino sulfo acid.

4. The composition of claim 1, wherein AS is p-amino benzoic acid.

5. A method of protecting human skin against actinic radiation, comprising the step of applying to the skin a dermatologically acceptable inert carrier containing an effective amount of a compound having the formula:

wherein the nucleoside is a glycoside of a compound selected from the group consisting of adenine, guanine, cytosine, uracil and thymine; Me is a cation selected from the group consisting of hydrogen, an alkali metal, and ammonium; $n$ is an integer from 1 to 3; $m$ is an integer from 1 to $(n + 1)$; and AS is an acid having from 1 to 20 carbon atoms and selected from the group consisting of an amino carboxyoic acid and an amino sulfo acid.

6. The method of claim 5, where AS is selected from the group consisting of an alkali metal salt of an amino carboxylic acid, and alkali metal salt of an amino sulfo acid, an ammonium salt of an amino carboxylic acid and an ammonium salt of an amino sulfo acid.

7. The method of claim 5, wherein AS is p-aminobenzoic acid.

* * * * *

UNITED STATES PATENT AND TRADEMARK OFFICE
CERTIFICATE OF CORRECTION

PATENT NO. : 3,937,809
DATED : February 10, 1976.
INVENTOR(S) : OTTO K. JACOBI

It is certified that error appears in the above-identified patent and that said Letters Patent are hereby corrected as shown below:

Column 1, line 58, Cancel "hanad" and substitute therefor ---hand---, Column 2, line 2, Cancel "of", second occurrence, and substitute therefor ---or---, Column 2, line 12, AFter "can" insert ---be---, Columns 3, 4, 5 and 6, TABLE I, Items No.1 through No.22, under the head Extinction Coefficient, cancel "$\lambda$", in each instance, Column 7, line 34, Cancel "of" and substitute therefor ---or---, Column 8, line 68, After "is" insert ---an---, Column 10, line 9, Claim 5, Cancel "carboxyoic" and substitute therefor ---carboxylic---.

Signed and Sealed this eighteenth Day of May 1976

[SEAL]

Attest:

RUTH C. MASON
Attesting Officer

C. MARSHALL DANN
Commissioner of Patents and Trademarks